United States Patent [19]

Hansen

[11] Patent Number: 4,491,232

[45] Date of Patent: Jan. 1, 1985

[54] SECURED SAMPLING FACILITY

[76] Inventor: Steven D. Hansen, 458 Shady Ct., Brea, Calif. 92621

[21] Appl. No.: 606,165

[22] Filed: May 2, 1984

[51] Int. Cl.³ .................. G01F 15/18; B65D 25/24
[52] U.S. Cl. ................................. 220/18; 220/4 C; 73/201
[58] Field of Search .............. 220/18, 4 A, 4 C, 1 T; 73/201

[56] References Cited

U.S. PATENT DOCUMENTS

| 845,226 | 2/1907 | Ford | 73/201 |
| 1,832,852 | 11/1931 | Bassett | 73/201 |
| 2,724,968 | 11/1955 | Greene | 220/18 X |
| 2,814,409 | 11/1957 | Perez | 220/4 C |
| 2,907,486 | 10/1959 | Perez | 220/4 C |
| 3,961,528 | 6/1976 | Ford | 73/201 |

Primary Examiner—Steven M. Pollard
Attorney, Agent, or Firm—Gene W. Arant; Paul H. Ware

[57] ABSTRACT

Structure and method for prevention of unauthorized access to effluent monitoring stations or the like.

2 Claims, 4 Drawing Figures

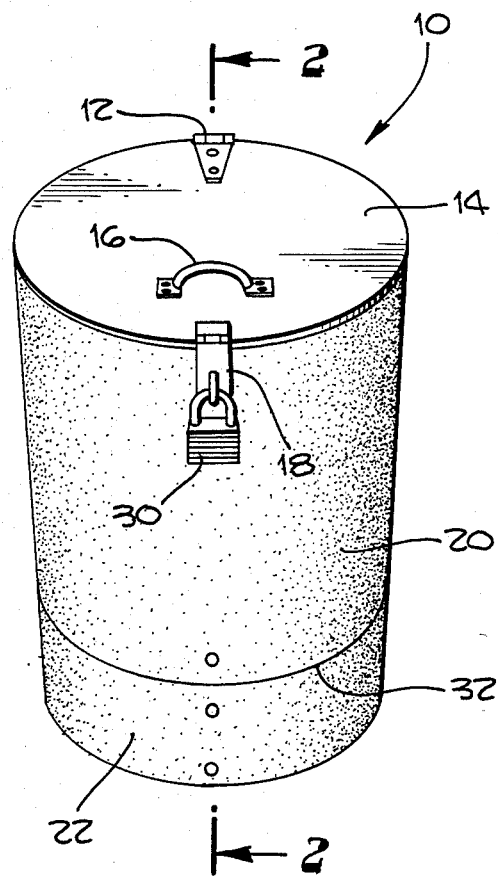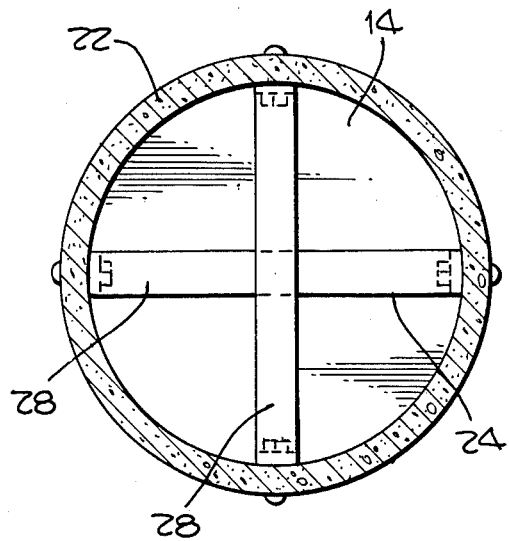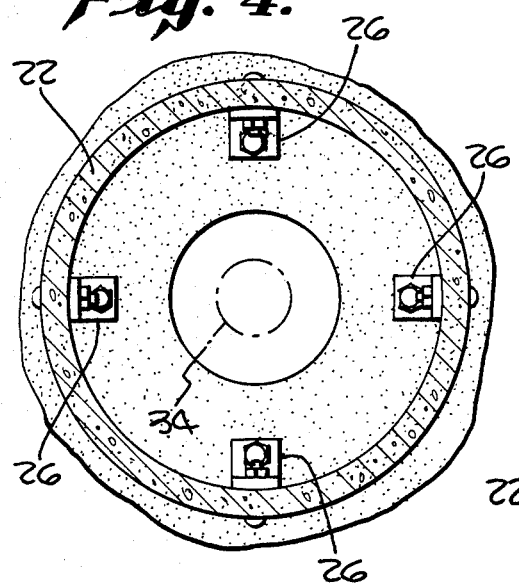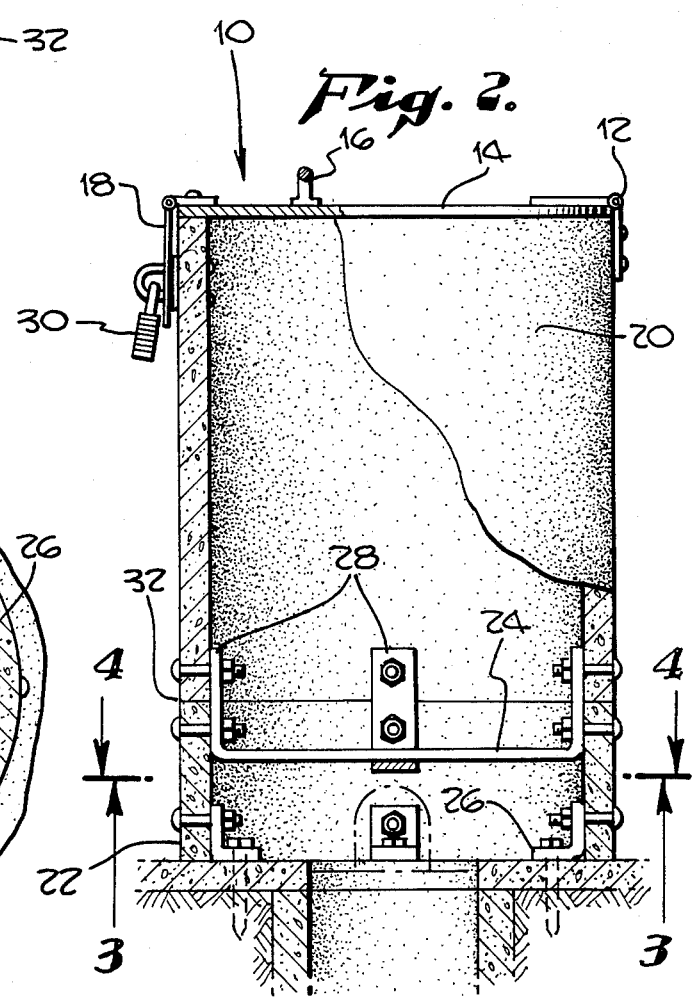

SECURED SAMPLING FACILITY

BACKGROUND OF THE INVENTION

Field of the Invention

This invention relates generally to localization and prevention of unauthorized access to effluent monitoring stations and more particularly to secured sampling facilities on waste water discharge into a sewer system.

Regulations of the U.S. Environmental Protection Agency and other regulating agencies, limit the amounts of pollutants that polluting facilities may discharge into streams or to publicly-owned treatment works. Examples of such controlled and regulated facilities are furnished by the electroplating and metal-finishing industrial installations.

In order to comply with promulgated ordinances and rules and regulations and to ensure tamper-proof operations, the installation of a secured sampling facility such as is contemplated by the present invention is essential. Many political subdivisions require periodic reports to be made by the polluting facility to indicate the nature and concentration of all regulated pollutants. Installations of secured sampling facilities such as contemplated by the present invention, therefore, have been required in order to insure compliance with standards and ordinances and regulations.

It would therefore be a great advantage to provide a secured sampling facility that is easy to install, economical to fabricate and that will provide the necessary tamper-proof security required.

It is therefore an object of the present invention to provide a secured sampling facility that is simple and inexpensive to fabricate.

It is a further object of the present invention to provide said facility in an easy-to-install device.

Still another object is to provide the foregoing objects in a facility that insures the integrity of the security so that tampering is prevented or it is readily apparent when tampering has taken place.

In the accomplishment of these and other objects a secure sampling facility has been provided in which the local site of a sample box, cleanout or sewer inspection station may be isolated and protected from unauthorized access. Authorized access is readily accomplished by the novel advantages of the invention while unauthorized entry may be prevented or readily detected.

BRIEF DESCRIPTION OF THE DRAWINGS

Further advantages and features of the present invention will be more fully apparent to those skilled in the art to which the invention pertains from the ensuing detailed description thereof, regarded in conjunction with the accompanying drawings wherein like reference characters refer to like parts throughout and in which:

FIG. 1 is an idealized perspective of a secured sampling facility such as is contemplated by the invention.

FIG. 2 is a cross section of a side elevation taken along line 3—3 of FIG. 2 showing the internal elements of the device.

FIG. 3 is a cross section of a plan elevation showing the orientation of the internal parts. (U-shaped brackets)

FIG. 4 is a cross section of a plan elevation taken along line 4—4 of FIG. 2.

DETAILED DESCRIPTION

Although a specific embodiment of the invention will now be described with reference to the drawings, it should be understood that the embodiment shown is by way of example only and merely illustrative of but one of the many possible specific embodiments which can represent applications of the principles of the invention. Various changes and modifications, obvious to one skilled in the art to which the invention pertains, are deemed to be within the spirit, scope and contemplation of the invention as further defined in the appended claims.

Referring to FIG. 1 with greater particularity, a secured sampling facility, denoted generally by the numeral 10, is shown in idealized perspective. A hinge 12 allows cover 14 to be raised by use of access handle 16 when padlock 30 is unlocked and hasp 18 is freed. Numeral 32 denotes the interface between top pipe section 20 and bottom pipe section 22. The secured sampling facility may be fabricated, for example, from a reinforced concrete shell, being two sections of pipe wherein a top pipe section may be about 30 inches in height and about 31 inches in diameter and a bottom pipe section, of the same diameter, may be about 12 inches in height.

Installation of the secured sampling facility may be more readily explained with reference to FIG. 2. Bottom pipe section 22 is bolted in place to existing concrete by means of at least two and preferably about four or more securing brackets 26. Placement of bottom section 22 is so as to enclose an existing sample box, cleanout or sewer inspection station 34. Two U-shaped brackets 28 may be attached to bottom pipe section 22 in upright, perpendicular orientation to each other so that they form a basket or shelf 24, for support of measuring instrumentation, called a monitoring shelf and so that the arms of the U-shaped brackets protrude above the top of bottom section 22.

Circular cover 14, of about the same diameter as top pipe section 20, preferably has been secured to top section 20 by means of hinge 12 and hasp 18 before delivery to the field. The bottom portion of top section 20 may be secured to bottom section 22 by means of U-shaped brackets 28 which will be bolted to both top and bottom sections 20 and 22 respectively. Upon locking padlock 30 into hasp 18, the facility will be secure upon the facility to be localized.

FIG. 3 shows the placement of U-shaped brackets 28 in relation to each other so as to form monitoring shelf 24 as support, for example, of a ph meter or other measuring instrumentation for determination of character, amount and/concentration of pollutants.

Thus there has been described a secured sampling facility that will maintain the integrity of the sampling site in preventing intrusion by unauthorized persons or animals and that will protect the site from the weather. Easy access is provided to authorized personnel to take readings or to perform any necessary and/or required operations. The secured sampling facility is easy to install and maintain, economical to fabricate and reliable for its intended purpose.

It is pointed out that although the present invention has been shown and described with reference to a particular embodiment, nevertheless various changes and modifications, obvious to one skilled in the art to which the invention pertains, are deemed to lie within the purview of the invention.

I claim:
1. A secured sampling facility comprising:
a bottom pipe section;
at least two securing brackets for securing said bottom pipe section in place;
a pair of U-shaped brackets, each having its bottom portion of sufficient length so that the upright arms of said U-shaped brackets fit along the inside of said bottom pipe section and located perpendicular to each other in said bottom pipe section so that the top portions of said U-shaped brackets protrude above the top of said bottom pipe section;
a top pipe section of the same diameters as said bottom pipe section and adapted to fit in interfaced relation therewith and so as to be attached thereto by means of said top portions of said U-shaped brackets that protrude above the top of said bottom pipe section;
a monitoring shelf for supporting measuring instrumentation formed by the orientation of said U-shaped brackets;
a circular cover secured to said top pipe section by means of a hinge and a hasp located in diametric opposition to each other, said cover having an access handle providing for easy access to the interior of said secured sampling facility; and
a padlock 30 for securing said circular cover to said top pipe section when it is desired to prevent access to the interior of said secured sampling facility.

2. A method of providing a secured sampling facility comprising the steps of:
selecting a bottom section of pipe;
attaching four brackets to said bottom section of pipe at equiangular distances about the interior periphery thereof;
selecting a location to be isolated;
driling holes at said location for the attachment of said brackets thereto;
bolting said bottom section of pipe by means of said holes at said location;
selecting a pair of U-shaped brackets having their bottom portions of a length such that their upright arms will fit slidably along the interior diameter of said bottom section of pipe;
attaching said U-shaped brackets in perpendicular relation to each other to said bottom section of pipe so that the top portions of said brackets protrude above the top of said bottom section of pipe;
selecting a top section of pipe;
selecting a circular cover of about the same diameter as said top section of pipe;
hingedly attaching said circular cover to one end of said top section of pipe;
selecting a hasp assembly having a hinge part and a loop part;
attaching said hinge part of said hasp assembly to said circular cover;
attaching said loop part of said hasp assembly to said top section of pipe in register with said hinge part of said hasp assembly; and
fastening the other end of said top section of pipe to said U-shaped brackets by means of the portions of said brackets which protrude above the top of said bottom section of pipe and so that said top section of pipe is in circumferential registry with said bottom section.

* * * * *